United States Patent
Pariseau et al.

(10) Patent No.: US 9,140,638 B2
(45) Date of Patent: Sep. 22, 2015

(54) PULSE DISCRIMINATOR FOR PARTICLE COUNTER

(71) Applicant: Particles Plus, Inc., Canton, MA (US)

(72) Inventors: David Pariseau, Los Altos, CA (US); Ivan Horban, Grants Pass, OR (US)

(73) Assignee: Particles Plus, Inc., Stoughton, MA (US)

( * ) Notice: Subject to any disclaimer, the term of this patent is extended or adjusted under 35 U.S.C. 154(b) by 0 days.

(21) Appl. No.: 14/214,907

(22) Filed: Mar. 15, 2014

(65) Prior Publication Data

US 2014/0268140 A1  Sep. 18, 2014

Related U.S. Application Data

(60) Provisional application No. 61/794,084, filed on Mar. 15, 2013.

(51) Int. Cl.
*G01N 15/02* (2006.01)
*G01N 15/14* (2006.01)

(52) U.S. Cl.
CPC ........ *G01N 15/0205* (2013.01); *G01N 15/1429* (2013.01); *G01N 15/1459* (2013.01); *G01N 2015/0238* (2013.01); *G01N 2015/1486* (2013.01)

(58) Field of Classification Search
CPC .......... G01N 15/0205; G01N 15/0211; G01N 15/1459; G01N 2021/4716; G01N 15/1434
USPC ...................................................... 356/335
See application file for complete search history.

(56) References Cited

U.S. PATENT DOCUMENTS 4,276,472 A * 6/1981 Costantino et al. ....... 250/214 B

FOREIGN PATENT DOCUMENTS

GB           674265 A  *  6/1952 ................. 595/50

* cited by examiner

*Primary Examiner* — Tarifur Chowdhury
*Assistant Examiner* — Md Rahman

(57) ABSTRACT

An airborne, gas, or liquid particle sensor with a pulse discriminator. The pulse discriminator provides greater qualification of signals associated with detected particulate signals.

5 Claims, 4 Drawing Sheets

PULSE DISCRIMINATOR FOR PARTICLE COUNTER

CROSS-REFERENCE TO RELATED APPLICATION

This application claims priority to U.S. Provisional Application Ser. No. 61/794,084 filed on Mar. 15, 2013, titled PULSE DISCRIMINATOR FOR PARTICLE COUNTER by inventors David Pariseau and Ivan Horban, the entire disclosure of which is hereby incorporated herein by reference.

This application is related to and incorporates by reference U.S. Non-Provisional application Ser. No. 14/214,899, filed herewith on Mar. 15, 2014, titled PARTICLE COUNTER WITH INTEGRATED BOOTLOADER by inventor David Pariseau; U.S. Non-Provisional application Ser. No. 14/214,870, filed herewith on Mar. 15, 2014, titled PERSONAL AIR QUALITY MONITORING SYSTEM by inventors David Pariseau and Adam Giandomenico; U.S. Non-Provisional application Ser. No. 14/214,903, filed herewith on Mar. 15, 2014, titled MIXED-MODE PHOTO-AMPLIFIER FOR PARTICLE COUNTER by inventors David Pariseau and Ivan Horban; U.S. Non-Provisional application Ser. No. 14/214,876, filed herewith on Mar. 15, 2014, titled MULTIPLE PARTICLE SENSORS IN A PARTICLE COUNTER by inventor David Pariseau; U.S. Non-Provisional application Ser. No. 14/214,889, filed herewith on Mar. 15, 2014, titled INTELLIGENT MODULES IN A PARTICLE COUNTER by inventor David Pariseau; and U.S. Non-Provisional application Ser. No. 14/214,895, filed herewith on Mar. 15, 2014, titled PULSE SCOPE FOR PARTICLE COUNTER by inventor David Pariseau.

BACKGROUND

Particle counters have been used for decades in manufacturing or industrial applications to measure particulate quantities in air, gases or liquids. Typically such counters would also bin particulates by size. These size bins vary by application and often by instrument. A particle counter has at least one size channel and popular counters can have 6 or more channels. Typically these size channels discriminate pulses based on the pulse height of the incoming signal. The pulse height refers to the peak voltage of the signal. These systems provide a go/no-go qualification for an incoming pulse, typically they are implemented in hardware and provide a simple gate function such that pulses below a minimum duration are excluded from counting. The intent is to reject noise, typically at the most sensitive resolution where the signal-to-noise ratio is the poorest. Therefore, was is needed is a system and method that allows for more accurate measurements of particles.

SUMMARY

In accordance with the various aspects of the present invention, a system and method are provided for more accurate measurements of particles. The foregoing is a summary and thus includes, by necessity, simplifications, generalizations and omissions of detail. Those skilled in the art will appreciate that the summary is illustrative only and is not intended to be in any way limiting.

BRIEF DESCRIPTION OF THE DRAWINGS

The foregoing summary as well as the following detailed description is better understood when read in conjunction with the appended drawings. For the purpose of illustrating the invention, there is shown in the drawings exemplary constructions of the invention; however, the invention is not limited to the specific various aspects, embodiments, methods and instrumentalities disclosed in the drawings.

DETAILED DESCRIPTION

Figure 1:
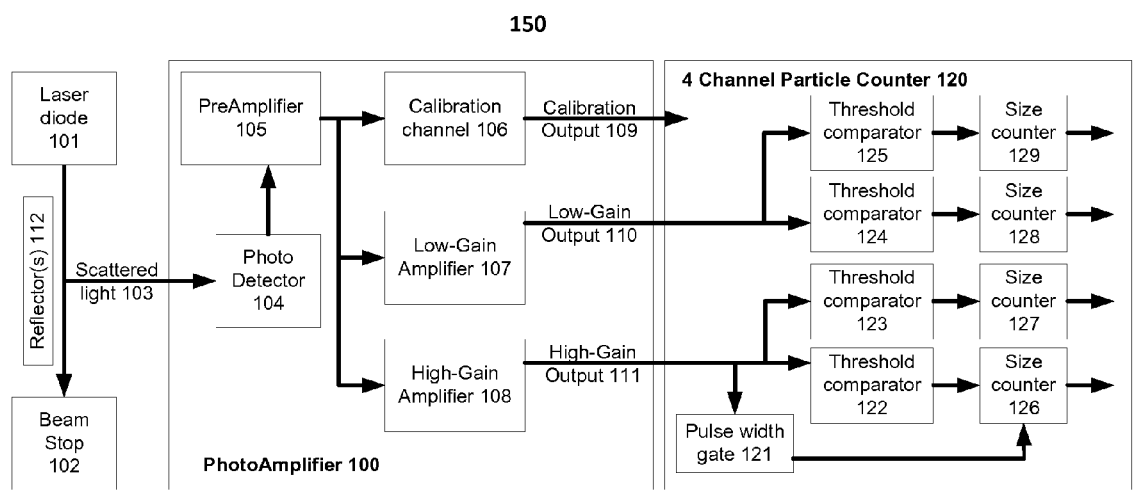
FIG. 1 shows a system in accordance with the various aspects of the present invention.

It is noted that, as used in this description, the singular forms "a," "an" and "the" include plural referents unless the context clearly dictates otherwise. Reference throughout this specification to "one aspect," "another aspect," "at least one aspect," "various aspects," "further aspect," "one embodiment," "an embodiment," "certain embodiments," or similar language means that a particular aspect, feature, structure, or characteristic described in connection with the embodiment or embodiments is included in at least one aspect or embodiment of the present invention. Thus, appearances of the phrases "in accordance with one aspect," "in accordance with various aspects," "in accordance another aspect," "one embodiment," "in at least one embodiment," "in an embodiment," "in certain embodiments," and similar language throughout this specification may, but do not necessarily, all refer to the same embodiment.

In accordance with the various aspects of the present invention, a device includes a computing device. As referred to herein, the devices may be part of a system or the system. It may be implemented to include a central processing unit (e.g., a processor), memory, input devices (e.g., keyboard and pointing devices), output devices (e.g., display devices), and storage device (e.g., disk drives). The memory and storage device are computer-readable media that may contain instructions or code that, when executed by the processor or the central processing unit, cause the device to perform certain tasks. In addition, data structures and message structures may be stored or transmitted via a data transmission medium, such as a signal on a communications link. Various communications channels may be used (e.g., the Internet, a local area network (LAN), a wide area network (WAN), or a point-to-point dial-up connection, or any other wireless channel or protocol) to create a link.

In accordance with the various aspects of the present invention, the device or system may be use various computing systems or devices including personal computers, server computers, hand-held or laptop devices, multiprocessor systems, microprocessor based systems, programmable consumer electronics, network personal computers (PCs), minicomputers, mainframe computers, distributed computing environments that include any of the above systems or devices, and the like. In accordance with the various aspects of the present invention, the device or system may also provide its services to various computing systems such as personal computers, cell phones, personal digital assistants, consumer electronics, home automation devices, and so on.

In accordance with the various aspects of the present invention, the device or system may be described in the general context of computer-executable instructions, such as program modules or code, which is executed by one or more computers or devices. Generally, program modules include routines, programs, objects, components, data structures, and so on that perform particular tasks or implement particular data types. Typically, the functionality of the program modules may be combined or distributed as desired in various embodiments.

Where a range of values is provided, it is understood that each intervening value, to the tenth of the unit of the lower limit unless the context clearly dictates otherwise, between the upper and lower limit of that range and any other stated or intervening value in that stated range, is encompassed within the aspects of the present invention. The upper and lower limits of these smaller ranges may independently be included in the smaller ranges and are also encompassed within the aspects of the present invention, subject to any specifically excluded limit in the stated range. Where the stated range includes one or both of the limits, ranges excluding either or both of those included limits are also included in the aspects of the present invention.

Referring now to FIG. 1, illustrated an implementation of system 150, also referred to as "particle counter system," having four channels. In this example a beam present between the laser diode (101) and the beam stop (102) scatters light (103) as particles cross that beam. Typically the scattered light (103) is focused by one or more reflectors (112) onto the face of a photo-diode (104) on a photo-amplifier board (100). The tiny current in the photo-diode is then pre-amplified, usually by a trans-impedance amplifier (105). The pre-amplified signal is usually available on a calibration channel (106) for use during calibration. The pre-amplifier (105) signal is also sent to one or more amplifiers. In this case there are two, a low-gain channel (107) and a high-gain channel (108). These amplifiers further increase the signal amplitude and transmit send it, often, to a separate particle counting board (120).

On this board the incoming pulse signals are sorted into size bins. In this example there are four channels, two channels (122, 123) connected to the high-gain amplifier (111) and two channels (124, 125) connected to the low-gain amplifier (110). The threshold comparators (122, 123, 124, 125) are setup during the calibration phase so that they each channel counts pulses above some threshold. This can be a manual process with manual adjustment of a potentiometer, or a programmatic process where firmware would set a digital potentiometer or digital-to-analog converter. The counter outputs (126, 127, 128, 129) would then be read by microcontroller and displayed to the user.

A similar system functions for gases other than air, and liquids. It also functions for counters that use a light-blocking rather than a light-scattering architecture, except that pulses in light-blocking systems see a decrease in light as the particles pass through the beam.

Figure 2:
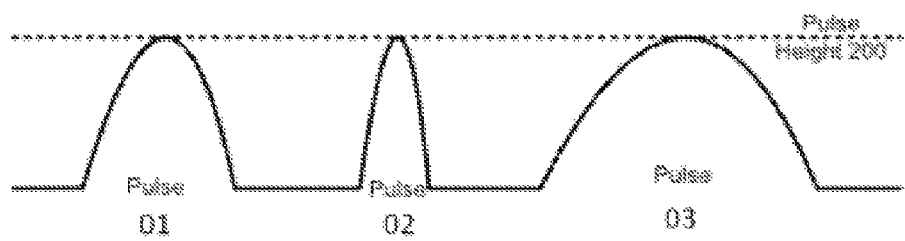
FIG. 2 shows a graph of pulses and height as related to various aspects of the present invention.

Referring now to FIG. 2, in accordance with certain aspects and embodiments, the qualification of all pulses is one-dimensional. Pulses (01,02,03) that each has the same pulse height (200) are all binned into the same size bin. A different amount of light is scattered in each case; some particle counters bin all of these pulses together. This architecture assumes that all pulses with the same pulse-height have a reasonably tight distribution of pulse-widths, so that the pulse-width can be ignored. In reality that may not in fact be the case. This one-dimensional approach of relying on a single parameter to size particles can introduce inaccuracy into the particle counter's results.

Referring again to FIG. 1, in accordance with certain aspects and implementations, the particle counter has a qualification for pulse width, alternatively or in combination a qualification for time-of-flight. In some embodiments, the particle counter includes a pulse-width gate (121), to further qualify incoming pulses. If placed on the most sensitive channel (122), pulses shorter than a minimum duration at the size counter (126) can be ignored and those that that have a minimum pulse-width are measured. Since the signal-to-noise ratio of the signal on this channel is typically poorest, this qualification helps to further discriminate true pulse signals from system noise.

In certain embodiments, pulse-width measurement is added for incoming pulses, which are in turn presented to the counter logic. Having two-dimensions (e.g., pulse height and pulse width) for each pulse provides the means to do things previously impossible with conventional particle counters.

The pulse width is used to ignore pulses that don't have an acceptable width threshold for a given threshold comparator. Here, the particle counter uses the two-dimensional characteristics of the pulse to make further determinations, such as:

ignore recycled pulses, by ignoring pulses longer than a maximum width threshold;

ignore noise, by ignoring pulses shorter than a minimum width threshold;

ignore interference from adjacent channels, by narrowing the acceptable pulse-width window; and perform more detailed analysis for a channel, by setting threshold for multiple channels to the same value but varying the pulse-width window for each.

In certain embodiments, the architecture for a particle counter is further extended by adding a peak pulse-height measurement for each pulse and multiplying pulse-height by pulse width to arrive at an estimate of a pulse-energy for each pulse. The pulse-energy of valid pulses is used to increment the appropriate counter for a size channel. This gives a better sizing result if the pulse-width vs. pulse height varies substantially for particles of a given size. The pulse-energy could also be used to qualify pulses of a given height as valid or invalid.

Figure 3:
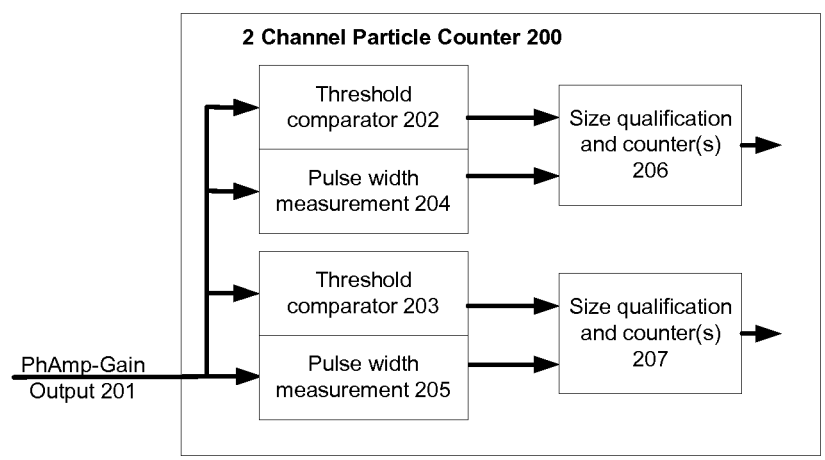
FIG. 3 shows a system in accordance with the various aspects of the present invention.

Referring to FIG. 3, in accordance with certain aspects and embodiments, the particle counter (200), also referred to as particle counter system (200), has two size qualification and counters, also referred to as "size qualifier" (206,207) that are supplied from a single photo-amplifier output (201). Alternatively, the particle counter (200) includes more or fewer channels, or is connected to photo-amplifiers with more outputs. The photo-amplifier output in this example (201) enters the counter front-end at which point pulses are presented to the threshold comparators (202, 203). The pulse-width is measured by both channels (204, 205) at the same time as the pulses are presented to the threshold comparators (202, 203), which allows for "pulse-width discrimination". The pulse width is measured in any of a number of ways. An example of measurement includes measuring the time the pulse spends above the threshold for a given channel. Other forms of measurement are also contemplated. After the pulse width is measured, the size qualification and counter (206,207) qualifies the pulse based on the width and increment the counter, if it is within a valid window.

Figure 4:
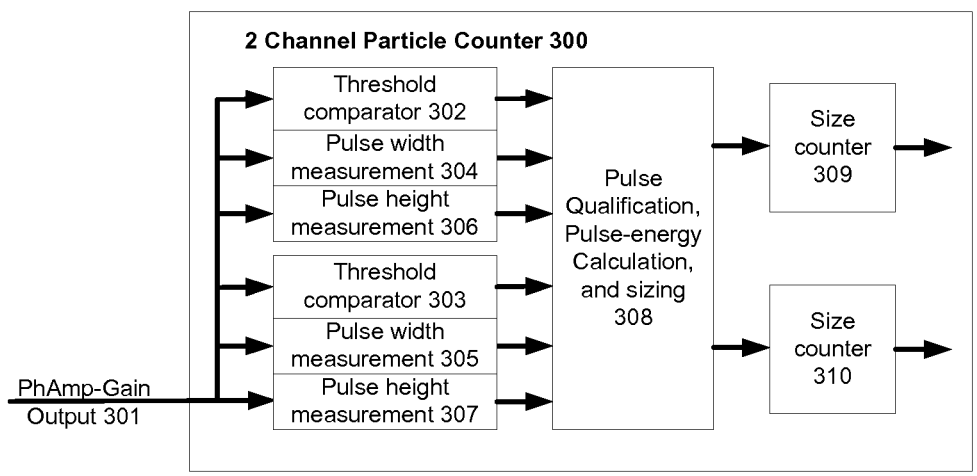
FIG. 4 shows a system in accordance with the various aspects of the present invention.

In certain embodiments of particle counter 200, pulses that satisfy a criterion of one or more threshold comparators (202, 203) can have one or more of the following behaviors:

have a minimum pulse-width threshold, and ignore pulses below this threshold;

have a maximum pulse-width threshold, and ignore pulses above this threshold;

have a normal pulse counter and count pulses above minimum and below maximum thresholds;

have an additional counter to count pulses below the minimum pulse-width threshold; and have an additional counter to count pulses above the maximum pulse-width threshold, Referring now to FIG. 4, in accordance with certain aspects and embodiments, the particle counter (300), also referred to as "particle counter system (300)", has an input supplied from a single photo-amplifier output (301). Alternatively, the particle counter (300) has more or fewer channels, or is connected to photo-amplifiers with more outputs. The photo-amplifier output (301) in this example enters the counter front-end at which point pulses are presented to the threshold comparators (302, 303). The pulse-width is measured by both channels (304, 305), at the same time as the pulses are presented to the threshold comparators (302,303), which also for "pulse-width discrimination". The pulse width is measured in any number of ways. An example of measurement includes measuring the time the pulse spends above the threshold for a given channel. The peak pulse-height is also measured for both channels (306,307), for example, at the same time as the pulse-width measurement above. The peak pulse height is captured by a peak-detector and converted by an analog-to-digital converter.

After both pulse-width and pulse-height have been measured for a given pulse these values are passed to post-processing circuitry (308). In certain embodiments, the post-processing circuitry (308) performs a number of operations, including but not limited to:

qualify pulses for a given threshold by pulse-width, as per pervious embodiment;

approximate pulse-energy by multiplying pulse-height by pulse-width, for qualified pulses;

size particles by pulse-energy instead of pulse-height, which may lead to better sizing;

implement an algorithm, which uses pulse-height and pulse-width to account for variations in air velocity within the airstream in order to bin particles by size, which could yield better sizing;

have fewer threshold comparators and more size channels, since the actual pulse-height is measured it allows us to create many more counter channels since we don't need dedicated comparators for each;

allows us to create multiple counters for a given pulse-height, or narrow range of heights, and discriminate pulses more carefully within this range, by pulse-energy or width or a combination of these;

allows us to perhaps process saturated signals from a single PhAmp-Gain stage, more on this below; and very flexible for setting up possible what-if scenarios and analyzing pulses.

A variation on the above embodiment would be to use a single Photo-Amp (301) output that would saturate for larger particle sizes. For this implementation, the optical design would be such as to ensure that larger particles would have reasonably consistent pulse-widths based on their size. To accomplish this the optical design might ensure that the beam was tightly collimated into a very thin ribbon. For such smaller particle sizes the discrimination would take place as previously described. For the larger size channels, the Gain output is saturating and the counter logic then bins the pulses based on their pulse width. This has the benefit of potentially providing a very large dynamic range instrument with a very limited (single output stage) front-end.

While various embodiments have been described above, it should be understood that they have been presented by way of example only, not limitation, and various changes in form and details may be made. Any portion of the device, instrument, apparatus and/or methods described herein may be combined in any combination, except mutually exclusive combinations. The aspects and embodiments described herein can include various combinations and/or sub-combinations of the functions, components and/or features of the different embodiments described. For example, multiple, distributed processing systems can be configured to operate in parallel.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

It will be apparent that various aspects of the present invention as related to certain embodiments may be implemented in software, hardware, application logic, or a combination of software, hardware, and application logic. The software, application logic and/or hardware may reside on a server, an electronic device, or be a service. If desired, part of the software, application logic and/or hardware may reside on an electronic device and part of the software, application logic and/or hardware may reside on a remote location, such as server.

In accordance with the aspects disclosed in the teachings of the present invention and certain embodiments, a program or code may be noted as running on a device, an instrument, a system, or a computing device, all of which are an article of manufacture. Additional examples of an article of manufacture include: a server, a mainframe computer, a mobile telephone, a multimedia-enabled smartphone, a tablet computer, a personal digital assistant, a personal computer, a laptop, or other special purpose computer each having one or more processors (e.g., a Central Processing Unit, a Graphical Processing Unit, or a microprocessor) that is configured to execute a computer readable program code (e.g., an algorithm, hardware, firmware, and/or software) to receive data, transmit data, store data, or perform tasks and methods. Furthermore, an article of manufacture (e.g., device) includes a non-transitory computer readable medium having a series of instructions, such as computer readable program steps or code, which is encoded therein. In certain aspects and embodiments, the non-transitory computer readable medium includes one or more data repositories, memory, and storage, including non-volatile memory. The non-transitory computer readable medium includes corresponding computer readable program or code and may include one or more data repositories. Processors access the computer readable program code encoded on the corresponding non-transitory computer readable mediums and execute one or more corresponding instructions. Other hardware and software components and structures are also contemplated.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, representative illustrative methods and materials are described herein.

All publications and patents cited in this specification are herein incorporated by reference as if each individual publication or patent were specifically and individually indicated to be incorporated by reference and are incorporated herein by reference to disclose and describe the methods and/or system in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A particle counter device comprising:
    at least one photo-amplifier;
    at least one threshold comparator in communication with the at least one photo-amplifier, the at least one threshold comparator triggers on pulses at a trigger level, which is above a noise floor;
    at least one peak-detector in communication with the at least one photo-amplifier, the at least one peak-detector provides a voltage for pulses above the trigger level that corresponds to a pulse-height of light scattered by a particle passing through a light-beam; and
    at least one pulse-width discriminator in communication with the at least one photo-amplifier, the at least one pulse-width discriminator provides a square-wave for pulses above the trigger level and represents a pulse-width, which includes a duration, of light scattered by the particle passing through the light-beam.

2. The particle counter device of claim 1, wherein both the pulse-height and the pulse-width are used to qualify pulses for a channel.

3. The particle counter device of claim 1, wherein the voltage is multiplied by the pulse-width's duration to derive a measure of pulse-energy, which approximates total light scattered by the particle passing through the light-beam.

4. The particle counter device of claim 3, wherein the pulse-energy measurement is used to qualify pulses for a channel.

5. The particle counter device of claim 3, wherein the pulse-energy measurement for a plurality of particles, over a period, is summed to provide a measure of total particle energy for the period.

* * * * *